United States Patent [19]

Krespan

[11] Patent Number: 4,474,700
[45] Date of Patent: Oct. 2, 1984

[54] β-SUBSTITUTED POLYFLUOROPROPIONATE SALTS AND DERIVATIVES

[75] Inventor: Carl G. Krespan, Wilmington, Del.

[73] Assignee: E. I. Du Pont DeNemours and Company, Wilmington, Del.

[21] Appl. No.: 380,016

[22] Filed: May 20, 1982

Related U.S. Application Data

[63] Continuation-in-part of Ser. No. 280,133, Jul. 2, 1981, abandoned.

[51] Int. Cl.$^3$ ............... C07C 117/00; C07C 121/38; C07C 121/00; C07C 121/413
[52] U.S. Cl. .................... 260/349; 521/38; 526/242; 526/243; 526/245; 526/248; 526/249; 260/465.4; 260/465.6; 260/501.15; 260/543 P; 260/544 F; 260/544 R; 260/941; 260/955; 560/150; 560/153; 562/605
[58] Field of Search ............... 260/349, 465.4

[56] References Cited

U.S. PATENT DOCUMENTS

| | | | |
|---|---|---|---|
| 2,802,028 | 8/1957 | England | 260/539 |
| 2,988,537 | 6/1961 | Wiley | 260/67 |
| 3,311,657 | 3/1967 | Graham | 260/539 |
| 3,311,658 | 3/1967 | Warnell | 260/544 |
| 3,532,725 | 10/1970 | Dorfman et al. | 260/404 |
| 3,535,351 | 10/1970 | Dorfman et al. | 260/404 |
| 3,557,165 | 1/1971 | Dorfman et al. | 260/404 |
| 3,853,720 | 12/1974 | Korach et al. | 204/98 |
| 4,127,731 | 11/1978 | Yamabe et al. | 560/192 |
| 4,131,740 | 12/1978 | England | 560/180 |
| 4,138,426 | 2/1979 | England | 260/465.6 |
| 4,164,463 | 8/1979 | Fang | 204/296 |
| 4,176,215 | 11/1979 | Molnar et al. | 521/27 |
| 4,273,728 | 6/1981 | Krespan | 260/465.6 |
| 4,273,729 | 6/1981 | Krespan | 260/543 F |
| 4,275,225 | 6/1981 | Krespan | 560/174 |
| 4,275,226 | 6/1981 | Yamabe et al. | 560/183 |
| 4,281,092 | 7/1981 | Breazeale | 526/247 |
| 4,330,654 | 5/1982 | Ezzell et al. | 526/240 |
| 4,337,211 | 6/1982 | Ezzell et al. | 260/456 F |
| 4,351,954 | 9/1982 | Muramatsu et al. | 260/349 X |

FOREIGN PATENT DOCUMENTS

| | | |
|---|---|---|
| 0011853 | 6/1980 | European Pat. Off. |
| 41736 | 12/1981 | European Pat. Off. |
| 0041735 | 12/1981 | European Pat. Off. |
| 0041737 | 12/1981 | European Pat. Off. |
| 0041738 | 12/1981 | European Pat. Off. |
| 7110532 | 1/1968 | Japan |
| 55-160007 | 12/1980 | Japan |
| 55-160008 | 12/1980 | Japan |
| 55-160029 | 12/1980 | Japan |
| 55-160030 | 12/1980 | Japan |
| 56-8151495 | 5/1981 | Japan |
| 1571356 | 7/1980 | United Kingdom |
| 2051831 | 1/1981 | United Kingdom |

OTHER PUBLICATIONS

Fieser and Fieser, "Organic Chemistry", 3rd ed., (1956), p. 167, Reinhold Pub. Corp., New York, N.Y.
Weygand & Hilgetag, "Preparative Organic Chemistry", (1972), p. 398, John Wiley & Son, New York, N.Y.
Kalb et al., Adv. Chem. Series, Amer. Chem. Soc. 129, (1973), pp. 13-26.
Banks, "Fluorocarbons and Their Derivatives", Elsevier, pp. 23 to 25 (1970).
England et al., J. Am. Chem. Soc., 80, pp. 6442 to 6446, (1958).
Ward, J. Org. Chem., 30, (1965), pp. 3009 to 3011.
Kato et al., J. Chem. Soc. Chem. Communications, 1173-1174, (1981).

Primary Examiner—Joseph Paul Brust
Attorney, Agent, or Firm—James A. Costello

[57] ABSTRACT

β-substituted polyfluoropropionate salts, derivatives and copolymers and processes for the preparation thereof.

12 Claims, No Drawings

β-SUBSTITUTED POLYFLUOROPROPIONATE SALTS AND DERIVATIVES

REFERENCE TO RELATED APPLICATION

This application is a continuation-in-part of U.S. Ser. No. 280,133, filed July 2, 1981, now abandoned.

TECHNICAL FIELD

This invention relates to β-substituted polyfluoropropionate salts and derivatives thereof, including copolymers.

It is known that various polyfluorinated propionates can be prepared from polyfluorinated olefins. For example, as disclosed in U.S. Pat. No. 2,802,028, $CF_2=CXY$, can be reacted with water and an alkali metal cyanide to yield a polyfluoramide and a polyfluoropropionate having the formula $HCXYCF_2CO_2M$, wherein, in both formulae, X is —F or —Cl, Y is —H, —F, —Cl, alkyl, cycloalkyl or alkyl substituted with F or Cl and M is an alkali metal. In this patent, the polyfluoronitrile $HCXYCF_2CN$, where X and Y are as above, is identified as a probable intermediate.

U.S. Pat. No. 3,311,657 discloses the reaction of fluoroolefins such as tetrafluoroethylene or chlorotrifluoroethylene with $CO_2$ and an alkali metal fluoride to give $CF_3CX'Y'CO_2M$ wherein X' can be —F and Y' is —Cl, —F or trifluoromethyl.

Kalb et al., in *Adv. Chem. Series Amer. Chem. Soc.* 129, 13 (1973), disclose the reaction of tetrafluoroethylene with $CO_2$ and potassium pentafluorophenoxide to yield $(C_6F_5)OCF_2CF_2CO_2K$.

Japanese Kokai 71 10532 discloses the preparation of various unfluorinated quaternary ammonium salts by reacting carboxylic esters with tertiary amines in the presence of phenols.

U.S. Pat. No. 3,535,351 discloses compounds of the formula $NC(CF_2)_aCO_2R$ wherein R is alkyl or aralkyl having 1-25 carbon atoms and a is 1-12. The conversion of the ω-cyanoperfluorinated alkanoate to $NC(CF_2)_aCO_2R'$ wherein R' is polyhaloalkyl is disclosed in U.S. Pat. No. 3,532,725.

Known polyfluoropropionate derivatives include $CN(CF_2)_aCOX''$, wherein X'' is —Cl, —F, —Br or —I and a is 1-12 which, as disclosed in U.S. Pat. No. 3,557,165, can be prepared from the polyhaloalkyl cyanoperfluorinated alkanoate described above. Banks, in "Fluorocarbons and Their Derivatives", Elsevier, p. 23 (1970) discloses the reaction of tetrafluoroethylene with alcohols, phenols, thiols, thiophenols and ketoximes in the presence of their sodium salts to yield 1:1 adducts thereof.

GB No. 2,051,831 A discloses substituted fluorocarbons having the formula $X(CF_2)_nY$ wherein X can be, e.g., a thioalkyl or thioester group and Y can be, e.g., a halide,

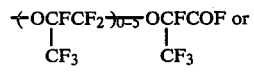
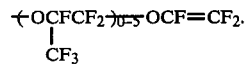

U.S. Pat. No. 4,275,226 depicts fluorocarbons having the formula $XR_FCF_2OCF=CF_2$ wherein X is —H, —Cl, —Br, —F, —CONRR', —COF, —$CO_2R$, —$SO_2F$ or —$PO(OR)_2$;
R is $C_{1-10}$ alkyl;
R' is —H or $C_{1-10}$ alkyl; and,
$R_F$ is a $C_{1-20}$ bifunctional perfluoro-containing group which can have one or more ether bonds. The compounds are stated to be prepared by heating the iodide, $XR_FCF_2OCF_2CF_2I$, in the presence of certain metals or organometallic compounds. The iodide is stated to be prepared from the acid fluoride, $XR_FCOF$, by reaction with tetrafluoroethylene, iodine and a metal halide. However, the patent fails to teach or suggest how to make various of the starting acid fluorides including those wherein X is $PO(OR)_2$. Consequently, the patent also fails in its disclosure of how to make the corresponding vinyl ether(s).

Warnell, U.S. Pat. No. 3,311,658, discloses $I(CF_2)_nCOF$, wherein n is 0-5, and hexafluoropropene adducts thereof, $I(CF_2)_n(CF_2OCF(CF_3))_{\overline{m}}COF$, wherein n is 0-5, and notes that the adduct can be converted to a vinyl ether-containing iodo compound.

Kato et al., in *J. Chem. Soc. Chem. Communications*, 1173 (1981), discloses the reaction $R_FI \rightarrow R_FP(O)(OC_2H_5)_2$ wherein $R_F$ is $C_{1-6}$ perfluoroalkyl.

In Japan Kokai No. 81 51,495, to Asahi Glass Co. Ltd., is disclosed the reaction

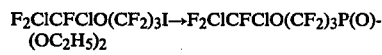

Kato, at the Fifth Winter Fluorine Conference, Daytona Beach, Fla., February 1981, disclosed the reaction disclosed in Kokai No. 81 51,495 and conversion of that product to the vinyl ether-containing phosphonate, $CF_2=CFO(CF_2)_3P(O)(OC_2H_5)_2$ and that the phosphonate can be converted to the phosphonyl chloride or the methyl phosphonate ester, which have the formula $CF_2=CFO(CF_2)_3P(O)Cl_2$ and $CF_2=CFO(CF_2)_3P(O)(OCH_3)_2$, respectively.

Ezzell et al., European Patent Application No. 41,736, disclose compounds having the formula

wherein
Y', as stated, can be —$SO_2Z'$, —$C(O)Z'$, or —$P(O)Z'_2$;
Z' is —OH, —OM, —OR, —F, —Br, —Cl or —I;
R is alkyl;
M is alkali metal or quaternary ammonium;
a and b are 0 or an integer; and,
$R_F$ and $R_F'$ are —F, —Cl, —$CF_3$ or —$CF_2Cl$.

The reference does not teach or suggest how to prepare the compound wherein Y' is —$PO(OR)_2$, —$P(O)Cl_2$ or —$P(O)F_2$.

Also disclosed in European Patent Application No. 41,736 is a derivative having the formula

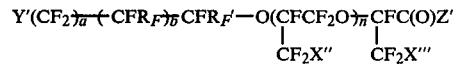

wherein
X'' is —F, —Cl or —Br;
X''' is —Cl or —Br; and
n is at least one.

Ezzell et al., European Patent Application No. 41,738 disclose a compound which is similar to the above derivative and has the formula

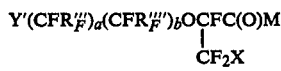

wherein $R_F'''$ and $R_F''''$ are —F, —Cl, perfluoroalkyl or fluorochloroalkyl;

X is —Cl, —I or —Br; and, a and b are 0 to 3 provided that $a+b=2$ or 3.

Ezzell et al., European Patent Application Nos. 41,737 and 41,735 disclose vinyl ethers which are derived from the derivative of 41,736 and have the formula

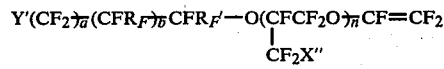

and copolymers derived therefrom. As in the other references by Ezzell et al., a procedure for preparing the compounds wherein Y' is —PO(OR)$_2$, —P(O)Cl$_2$ or —P(O)F$_2$ is not taught or suggested.

Korach et al., U.S. Pat. No. 3,853,720, disclose fluoropolymers, containing pendant acid groups, having ion exchange properties and being useful as diaphragm materials in electrolysis cells.

An object of this invention is to provide a novel polyfluoropropionate and a process for the preparation thereof. It is a further object to provide a novel derivative of the polyfluoropropionate as well as copolymerizable monomers prepared from the derivatives.

DISCLOSURE OF THE INVENTION

For further comprehension of the invention and of the objects and advantages thereof, reference may be made to the following description and to the appended claims in which the various novel features of the invention are more particularly set forth.

The invention resides in the process for preparing a β-substituted polyfluorinated propionate salt in which process a polyfluoroolefin having the formula $CF_2=CFY$ is mixed and reacted with $MX_n$ and $CO_2$ in a polar aprotic solvent at a temperature of about $-20°$ C. to about $150°$ C., wherein said formulae: X is —CN, —N$_3$, —SR, or —PO(OR')$_2$;

R is C$_{1-10}$ alkyl or aryl or alkaryl having no more than 10 carbon atoms;

R' is —CH$_3$, —C$_2$H$_5$, —CH$_2$CF$_3$ or —CH$_2$CF$_2$CF$_2$H;

Y is —Cl, —F, —Br or —OR$_F$, except that when X is —CN, Y is —Cl, —F or —Br;

R$_F$ is perfluoroalkyl, branched or linear, having 1-10 carbon atoms or such perfluoroalkyl having one or more carbon-carbon links interrupted by ether oxygen;

M is alkali metal, alkaline earth metal or quaternary ammonium, —NR$^1$R$^2$R$^3$R$^4$, wherein R$^1$-R$^4$ are, independently, C$_{1-6}$ linear alkyl, allyl or benzyl; preferably R$^1$-R$^4$ are methyl; and n is the valence of M and is 1 or 2.

The invention also resides in the β-substituted polyfluoropropionate salt which is prepared by the above-described process, and certain derivatives thereof; in processes for preparing derivatives; in a copolymer which is prepared from said derivatives; in a process for preparing a cyano-substituted fluorinated copolymer; and in molded objects of such copolymers, e.g., films. The β-substituted polyfluoropropionate salt has the formula:

where X is —CN, —N$_3$, —PO(OR')$_2$, —SR or —SO$_2$R, and Y, M and n are as defined above. The sulfone is derived from the thioether by oxidation, e.g., with hydrogen peroxide in the presence of acetic acid as described by Ward in *J. Org. Chem.* 30, 3009 (1965) and in Example 23.

The derivatives of the β-substituted polyfluoropropionate salt are substituted fluorocarbons which have the formula:

wherein

X' is —N$_3$, —SR, —SO$_2$R, —PO(OR')$_2$, —P(O)Cl$_2$ or —P(O)F$_2$;

R, R' and Y are as defined above;

Z is —COCl, —CO$_2$R'', —CO$_2$H,

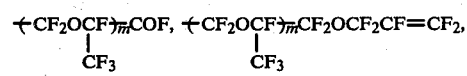

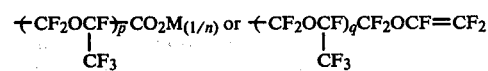

R'' is C$_{1-6}$ linear alkyl, allyl or benzyl; and m is 0-6; p is 1-6; and q is 0 or 1-5, provided that when Z is the CO$_2$M-containing group, X' is —N$_3$, —SR, —SO$_2$R, or —P(O)(OR')$_2$.

The copolymer of the invention contains repeat units which have the following formula:

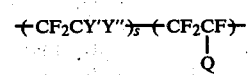

wherein Q is

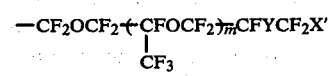

or

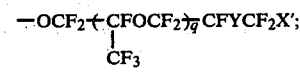

wherein

Y' is —F or —H;

Y'' is —F, —H, —Cl, —R$_F'$ or —OR$_F'$;

R$_F'$ is perfluoroalkyl having 1-4 carbon atoms;

s is about 2 to about 1000, preferably about 10 to about 200; and

Y, X', q and m are as defined above; q and m are preferably 0 or 1.

Molded objects of the copolymer include films. When X' is —PO(OR')$_2$, —P(O)Cl$_2$, —P(O)F$_2$, —SR, or —SO$_2$R, the film are chemically convertible to ion-exchange membranes.

In the process of preparing the salt of the invention, the reactants can be mixed in any order. Preferably, the reactants are mixed in the solvent at a low temperature, e.g., less than about −20° C., after which the mixture is heated to the reaction temperature of about −20° C. to about 150° C., preferably about 0° C. to about 100° C. By way of further example, CO$_2$ may be added to a mixture of MX$_n$ and solvent, followed by the introduction of the fluoroolefin at the reaction temperature, or, a mixture of MX$_n$ and solvent may be added to a mixture of CO$_2$ and the fluoroolefin at the reaction temperature. Reaction pressure is not critical. Preferably, the reaction pressure is about 100 psi to about 2000 psi (690 kPa–13,800 kPa).

Suitable solvents include, for example, dimethyl sulfoxide, acetonitrile, glymes such as mono-, di-, tri- and tetraethyleneglycol dimethyl ether, polyethylene oxide diethyl ethers, tetrahydrofuran, tetramethylene sulfone, dimethyl formamide, hexamethyl phosphoramide, tetraalkyl ureas and mixtures of the above.

The relative amounts of the reactants are not critical. Typically, the number of moles of CO$_2$ is greater than the number of moles of MX$_n$. The number of moles of the fluoroolefin is typically about the same as that of MX$_n$, although the fluoroolefin may be employed advantageously in mole ratios from about ½ to about 4/1, relative to MX$_n$.

The β-substituted polyfluorinated propionate salt of the invention may be collected in crude form after the reaction is terminated by removal of the solvent at low pressure. However, conveniently, the salt may also be converted to an ester which can be isolated by, e.g., distillation or washing with water. Conversion to the ester can be carried out by treating the reaction mixture with an alkylating agent such as methyl bromide, allyl bromide, ethyl iodide, dimethyl sulfate, methyl fluorosulfate or methyl p-toluenesulfonate.

The quaternary ammonium propionate salt of the invention, that is, the salt wherein M is —NR$^1$R$^2$R$^3$R$^4$, can also be prepared from esters of other propionate salts of the invention, said esters having the formula XCF$_2$CFYCO$_2$R$^4$ wherein X is —N$_3$, —SR, —SO$_2$R or —CN and Y, R and R$^4$ are as defined above, by reacting such an ester with an appropriate tertiary amine of the formula NR$^1$R$^2$R$^3$. Preparation of the quaternary ammonium propionate salt from a cyanoester, as described in Example 13A, is unexpected due to the tendency of nucleophiles to attack cyanoesters nonselectively.

The derivatives of the invention can be prepared by various procedures. For example, the fluorinated ester, i.e., X'CF$_2$CFYZ, wherein Z is —CO$_2$R'', can be prepared by treating the salt, in or apart from the reaction mixture, with an alkylating agent as described above.

The derivative wherein Z is —COCl or —COF (i.e.,

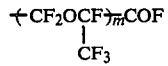

wherein m is 0) can be prepared by treating the propionate salt of the invention with a chlorinating agent such as thionyl chloride or phosphorous pentachloride to form the acyl chloride which may be further reacted with an appropriate fluoride salt, e.g., NaF, to form the acyl fluoride. The acyl fluoride can also be prepared by treating the propionate salt, preferably a quaternary ammonium propionate salt, with perfluoroallyl fluorosulfate, SF$_4$ or COF$_2$. The acyl halide wherein X' is —CN, and which therefore is not encompassed by the invention, can also be prepared by these procedures; if cyano group involvement occurs, the procedure described in U.S. Pat. No. 3,557,165 may be employed after converting the propionate salt to an ester.

The acyl fluoride can be converted to the derivative wherein Z is

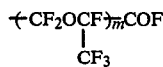

and m is 1 to 6 by reacting the acyl fluoride with hexafluoropropene oxide in the presence of fluoride ions as described, e.g., in U.S. Pat. No. 4,131,740. This derivative wherein X' is —N$_3$, —SR or —SO$_2$R, as well as the related cyano-functional derivative not of the invention, can also be prepared directly from the corresponding quarternary ammonium salt of the invention wherein X is —N$_3$, —SR, —SO$_2$R or —CN by reacting said salt with carbonyl fluoride followed by hexafluoropropene oxide. The quaternary ammonium salt optionally can be prepared in situ by reacting a fluoroester with a tertiary amine as described above. The derivative wherein Z is the fluorinated vinyl ether-containing group

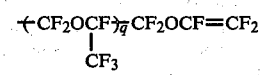

can be prepared by pyrolyzing the derivative wherein Z is

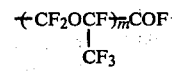

and m is at least one and preferably at least two, in an aprotic solvent in the presence of a carbonate, phosphate, sulfite or sulfate salt of an alkali or alkaline earth metal, preferably sodium carbonate or trisodium phosphate.

The derivative wherein Z is the above fluorinated vinyl ether-containing group can also be prepared by pyrolyzing the derivative wherein Z is

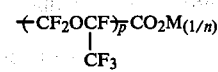

in the absence of solvent or added salts, as described below in Example 21. The latter derivative is prepared by alkaline hydrolysis of the corresponding acyl fluoride. By either method, a

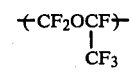

group is lost. Hence, m must be at least one and q is one less than m or p. hen pyrolyzing a derivative of the invention in which X' is —PO(OR')$_2$, R' is preferably —CH$_2$CF$_3$. Copolymers prepared from the vinyl ether-containing compound wherein q is at least one are preferred for use as ion-exchange membranes.

The derivative wherein Z is the fluorinated allyl ether-containing group

can be prepared by reacting the derivative wherein Z is

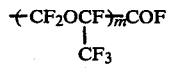

with perfluoroallylfluorosulfate or perfluoroallylchloride in the presence of fluoride ions as described in U.S. Pat. Nos. 4,273,728, 4,273,729 and 4,275,225.

The derivative wherein Z is the above fluorinated allyl ether-containing group and m is 0, as well as the related cyano-functional fluorinated allyl ether, i.e., wherein X' is —CN (not of the invention), can also be prepared directly from the quaternary ammonium propionate salt of the invention wherein X is —N$_3$, —SR, —SO$_2$R, —PO(OR')$_2$ or —CN by reacting the salt with perfluoroallylfluorosulfate as described in Example 13B, or, preferably, by reacting said quaternary ammonium propionate with carbonyl fluoride followed by perfluoroallylfluorosulfate as described in Examples 14 and 16. The quaternary ammonium salt optionally can be prepared in situ by reacting a fluoroester with a tertiary amine as described above.

The derivatives of the invention wherein Z is the above fluorinated vinyl or allyl ether-containing group, as well as the related cyano-functional fluorinated vinyl or allyl ether, i.e., wherein X' is —CN and which are not of the invention, are copolymerizable with fluoroolefins such as tetrafluoroethylene, chlorotrifluoroethylene, vinylidene fluoride, or mixtures thereof with hexafluoropropene or perfluoroalkyl vinyl ether such as CF$_2$=CFOR$_F'$ wherein R$_F'$ is perfluoroalkyl having 1-4 carbon atoms, as described below in Example 15 and in U.S. Pat. Nos. 4,273,728, 4,273,729 and 4,275,225.

The derivatives of the invention wherein X' is —P(O)Cl$_2$ can be prepared by the process of the invention wherein MX$_n$ is M[PO(OR')$_2$]$_n$ and treatment of the resulting salt with phosphorous pentachloride as described, for example, in Example 19, below. The derivative wherein X' is —P(O)F$_2$ can be prepared from the phosphonyl chloride by treatment with a fluoride salt, for example, NaF.

The copolymers of the invention, which are moldable into shaped articles, such as films, possess pendant functional groups, X', which confer special utility. Copolymers having pendant groups —PO(OR')$_2$, —P(O)Cl$_2$, —P(O)F$_2$, —SR or —SO$_2$R have ion-exchange properties after hydrolysis, the latter two groups requiring conversion to sulfonates or carboxylates as described by Ward in *J. Org. Chem.* 30, 3009 (1965). Use of fluoropolymers containing a pendant —PO(OR')$_2$, —P(O)Cl$_2$, sulfonate or carboxylate group as electrolysis cell diaphragm materials is disclosed in U.S. Pat. Nos. 4,164,463 and 3,853,720. Use of fluoropolymers containing pendant sulfonate or carboxylate groups as ion-exchange membranes is disclosed in U.S. Pat. No. 4,176,215.

Copolymers having pendant azido groups may be converted into chemically stable, structural foams by heating to a temperature at which N$_2$ is released, said gas serving as a blowing agent. Such copolymers may also be converted to useful cyano-containing copolymers by reaction of the pendant —CF$_2$N$_3$ groups with a tertiary phosphine such as triphenylphosphine.

Cyano-substituted copolymers, that is, copolymers wherein X' is —CN and which therefore are not copolymers of the invention, can be prepared from the vinyl or allyl ether-derived copolymer having a pendant nitrile group, that is, the copolymer wherein wherein Q is

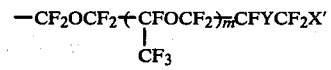

or

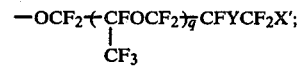

and X' is —N$_3$, by reacting the copolymer with a tertiary phosphine as illustrated below in Example 13D. The cyano-substituents provide cure sites for such copolymers, permitting their conversion to fluoroelastomers as described in European Patent Application No. 11,853, published Nov. 6, 1980. Useful perfluoroalkylenetriazine polymers are also derivable from cyano-functional propionate salts after conversion to the methyl esters, as described in U.S. Pat. Nos. 3,532,725 and 3,557,165. Pendant cyano groups may also be hydrolyzed by known methods to carbonyl and carboxyl salt groups, i.e., —CO$_2$H and —CO$_2$$^-$M$^+$, respectively, thus providing copolymers with ion-exchange properties.

Other fluoropolymers can be prepared indirectly from the propionate salt of the invention. For example, when X is —CN and Y is —F, the salt can be hydrolyzed with aqueous acid or aqueous alkali to tetrafluorosuccinic acid which can be further reacted with carbonyl fluoride, under the conditions described in U.S. Pat. No. 3,213,062 to yield perfluorobutyrolactone. Perfluorobutyrolactone is a useful intermediate to carboxylated perfluoropolymers as described in U.S. Pat. No. 4,127,731.

In the following Examples which are illustrative of the invention, all parts and percentages are by weight and temperatures are in °C. unless otherwise indicated. Examples 1-7 illustrate preparation of propionate salts of the invention, collected as esters thereof or converted to acids and collected as esters of the acids. Examples 8-11, 14 and 16-17 illustrate preparation of propionate salts of the invention and, except Example 16, conversion thereof to derivatives of the invention. Examples 12-13 illustrate preparation of propionate salts of the invention and conversion thereof to useful compounds not of the invention. Examples 15 and 22 illustrate preparation of copolymers of the invention. Examples 18-21 illustrate preparation of derivatives of the invention.

Preferred embodiments of the invention are illustrated by Examples 4B, 7, 8, 19A, 19C, the combination of Examples 20, 21 and 22 to prepare vinyl ether copolymers and the combination of Examples 16, 14B and 15 such that a tetramethylammonium salt is prepared as described in Example 16, except that the solvent is diglyme, then, in the same reaction vessel, said salt is converted to perfluoro-4-oxa-6-heptenyl azide as described in Example 14B which is copolymerized as described in Example 15 to prepare allyl ether copolymers.

EXAMPLE 1

A. Potassium 3-Cyanotetrafluoropropionate in Dimethyl Formamide and Tetrafluorosuccinic Acid and Esters $$KCN + CF_2=CF_2 + CO_2 \longrightarrow$$

$$NCCF_2CF_2CO_2^-K^+ \xrightarrow{H^+/H_2O} HO_2CCF_2CF_2CO_2H$$

A mixture of 26.0 g (0.40 mole) of KCN, 150 ml of dimethyl formamide, 50 g (0.50 mole) of tetrafluoroethylene (TFE), and 50 g of $CO_2$ was held at 50° for 4 hr., and then at 100° for 4 hr. at a maximum pressure of 1100 psi ($7.6 \times 10^3$ kPa). The resulting mixture was dark and contained no insoluble salts. Volatile compounds were removed from the mixture under reduced pressure leaving a viscous residue of potassium 3-cyanotetrafluoropropionate, which substantially solidified to a deliquescent semisolid when triturated with ether. IR (neat): 2288 (weak covalently bound CN), 1680 (strong $CO_2$), and 1250-1100 cm$^{-1}$ (C—F, C—O) with broad H-bonded OH at 3450 and weak saturated CH at 2940 cm$^{-1}$.

The residue was stirred at 25° for one day with a mixture of 300 ml of water and 110 ml of conc. $H_2SO_4$. Continuous extraction with ether for 30 hr. and evaporation of the ether extract gave a residue of crude tetrafluorosuccinic acid which was refluxed with 500 ml of absolute ethanol and 2 ml of conc. HCl for 18 hr. The water/ethanol mixture was distilled off, and the procedure was repeated with 400 ml of absolute ethanol and 5 ml of conc. HCl and again with 500 ml of absolute ethanol and 1 ml of conc. HCl. Distillation resulted in 19.5 g (20% based on KCN) of diethyl tetrafluorosuccinate, bp mostly 77° (7 mm). Identification by IR and $^{19}$F and $^1$H NMR was confirmed by a treatment with ammonia to form tetrafluorosuccinamide in 82% yield, mp 257°-260° (subl), which was not depressed upon admixture with authentic tetrafluorosuccinamide.

B. Potassium 3-Cyanotetrafluoropropionate in N,N′-Dimethylethyleneurea and Tetrafluorosuccinic Acid and Esters A 400 ml metal tube charged with 26.0 g (0.40 mole) of KCN, 150 ml of N,N′-dimethylethylene-urea, 50 g (1.1 mole) of $CO_2$, and 50 g of (0.50 mole) of tetrafluoroethylene was shaken at 50° for 4 hr. and then at 100° for 4 hr. Solvent, bp 40°-43° (0.1 mm, $1.3 \times 10^{-2}$ kPa), was distilled from the dark reaction mixture, and a partially crystalline residue of potassium 3-cyanotetrafluoropropionate was extracted twice with ether.

The residue was stirred at 60° for 3 days with 300 ml of $H_2O$ and 200 ml of conc. $H_2SO_4$. Continuous extraction of the resulting mixture with ether and evaporation of the extracts afforded crude tetrafluorosuccinic acid, which was refluxed for a day with 600 ml of absolute ethanol and 2 ml of conc. HCl. Distillation of the water/ethanol mixture was followed by addition of 500 ml of ethanol and 1 ml of conc. HCl. Slow distillation of solvent and fractionation of high boiling point compounds gave 12.9 g (13%) of diethyl tetrafluorosuccinate, bp 63°-67° (5 mm, $6.5 \times 10^{-1}$ kPa) identified by IR analysis.

EXAMPLE 2

Tetraethylammonium 3-Cyanotetrafluoropropionate in Acetonitrile and Tetrafluorosuccinic Acid and Esters $$(C_2H_5)_4NCN + CF_2=CF_2 + CO_2 \rightarrow NCCF_2CF_2CO_2^-N^+(C_2H_5)_4$$

A 400 ml tube charged with 52.1 g (0.33 mole) of tetraethylammonium cyanide, 150 ml of acetonitrile, 50 g (1.1 mole) of $CO_2$, and 50 g (0.50 mole) of tetrafluoroethylene was agitated at 50° for 4 hr. and then at 100° for 4 hr. The liquid reaction mixture was evaporated to give 96 g of residual viscous oil and solid tetraethylammonium 3-cyanotetrafluoropropionate.

A 48 g samples of the crude product was hydrolyzed at 70° with aqueous $H_2SO_4$. Tetrafluorosuccinic acid was extracted with ether and esterified with ethanol/HCl to give 16.6 g (41%) of diethyl tetrafluorosuccinate, bp 68°-70° (5 mm, $6.5 \times 10^{-1}$ kPa), identified by IR analysis.

EXAMPLE 3

Tetraethylammonium 3-Cyanotetrafluoropropionate in Acetonitrile and Methyl 3-Cyanotetrafluoropropionate $$(C_2H_5)_4NCN + CF_2=CF_2 + CO_2 \longrightarrow$$

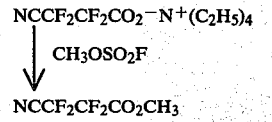

A 400 ml metal tube charged with 62.4 g (0.40 mole) of tetraethylammonium cyanide, 150 ml of acetonitrile, 33 g (0.75 mole) of $CO_2$ and 40 g (0.40 mole) of tetrafluoroethylene (TFE) was agitated at 100° for 8 hr. The pressure was maintained at 300 psi ($2.1 \times 10^3$ kPa) throughout. Evaporation of volatiles gave 110 g of a dark solid containing tetraethylammonium 3-cyanotetrafluoropropionate.

The solid was treated with 300 ml of diethyl ether and 45.6 g (0.40 mole) of methyl fluorosulfate. After 3 days the mixture was filtered, and most of the ether distilled off. The produce was transferred to a cold trap at 5 mm ($6.5 \times 10^{-1}$ kPa) and then fractionated to give 34.4 g (46%) of methyl 3-cyanotetrafluoropropionate, bp 95°-98°, identified by comparison of its IR spectrum with that of authentic methyl 3-cyanotetrafluoropropionate.

EXAMPLE 4

A. Sodium 3-Cyanotetrafluoropropionate in Dimethyl Sulfoxide and Methyl 3-Cyanotetrafluoropropionate A mixture of 19.6 g (0.40 mole) of NaCN, 33 g (0.75 mole) of $CO_2$, and 50 g (0.50 mole) of TFE in 150 ml of dimethyl sulfoxide (DMSO) was maintained at 100° for 1 hr. at about 700 psi ($4.8 \times 10^3$ kPa) to yield a dark liquid mixture which contained sodium 3-cyanotetrafluoropropionate.

The resulting mixture was stirred with 63 g (0.50 mole) of dimethyl sulfate until an initial mild exothermic reaction subsided, and then was heated at 60° for 1 hr. Volatile compounds in the mixture were removed by warming the mixture to 64° (5 mm, $6.5 \times 10^{-1}$ kPa). The volatiles were fractionated to give 43.1 g (58% based on NaCN) of methyl 3-cyanotetrafluoropropionate, bp 90°–96°, identified by IR.

B. Sodium 3-Cyanotetrafluoropropionate in DMSO at 25° and Methyl 3-Cyanotetrafluoropropionate A mixture of 24.5 g (0.50 mole) of NaCN, 33 g (0.75 mole) of $CO_2$, and 50 g (0.50 mole) of TFE in 150 ml of DMSO was maintained at 17°–25° for more than about 19 hr. while the pressure was allowed to drop from 600 to 250 psi ($4.1 \times 10^3$ to $1.7 \times 10^3$ kPa).

After being maintained at about 25° for 2 more days, the reaction mixture, which contained sodium 3-cyanotetrafluoropropionate, was treated with 69.3 g (0.55 mole) of dimethyl sulfate, stirred, and allowed to stand overnight. Fractionation of the volatile products gave 53.3 g (58%) of methyl 3-cyanotetrafluoropropionate, bp 90°–97°.

C. Sodium 3-Cyanotetrafluoropropionate in Tetraglyme and Methyl 3-Cyanotetrafluoropropionate A mixture of 24.5 g (0.50 mole) of NaCN, 33 g (0.75 mole) of $CO_2$, and 50 g (0.50 mole) of TFE in 150 ml of tetraglyme was maintained at 100° for 8 hr. at about 1330 to 1100 psi ($9.2 \times 10^3$ to $7.6 \times 10^3$ kPa) to give sodium 3-cyanotetrafluoropropionate.

Methylation of the product with 63.0 g (0.50 mole) of dimethyl sulfate yielded 35.8 g (39%) of methyl 3-cyanotetrafluoropropionate, bp 90°–96°, identified by IR.

EXAMPLE 5

Sodium 3-Cyanotetrafluoropropionate and Allyl 3-Cyanotetrafluoropropionate

The reaction of Example 4A to yield sodium 3-cyanotetrafluoropropionate was repeated and the reaction mixture was stirred with 48.4 g (0.40 mole) of allyl bromide for 2 hr. Volatile products were removed at 50° (5 mm, $6.7 \times 10^{-1}$ kPa) and fractionated to yield 29.9 g (35%) of allyl 3-cyanotetrafluoropropionate, bp 55° (50 mm, 6.7 kPa). IR ($CCl_4$): 3090 (unsaturated CH), 2960 and 2860 (saturated CH), 2260 (CN), 1785 (C=O), 1650 (C=C), and 1200–1100 cm$^{-1}$ (CF, C—O). NMR ($CCl_4$): $^1$H 5.6 (2$^{nd}$ order m, 3H=CH) and 4.92 ppm (d, $J_{HH}$ 5.4 Hz, 2H, $CH_2$); $^{19}$F −107.5 (t, $J_{FF}$ 5.8 Hz, 2F, $CF_2CN$) and −119.5 ppm (t, $J_{FF}$ 5.8 Hz, 2F, $CF_2C=O$).

Anal. Calcd. for $C_7H_5F_4NO_2$: C, 39.82; H, 2.39, N, 6.64. Found: C, 39.92; H, 2.49; N, 6.75.

EXAMPLE 6

Calcium 3-Cyanotetrafluoropropionate and Methyl 3-Cyanotetrafluoropropionate

A 400 ml metal tube charged with 23.0 g (0.25 mole) of $Ca(CN)_2$, 150 ml of DMSO, 33 g (0.75 mole) of $CO_2$ and 50 g (0.50 mole) of TFE was shaken at 50° for 6 hr. and at 100° for 4 hr. to give calcium 3-cyanotetrafluoropropionate.

The reaction mixture was then stirred with 69.3 g (0.55 mole) of dimethyl sulfate until an initial exothermic reaction subsided. Removal of volatiles under reduced pressure and distillation of the volatiles gave 14.6 g (16%) of methyl 3-cyanotetrafluoropropionate, bp 90°–97°.

EXAMPLE 7

Sodium 2-Chloro-3-cyanotrifluoropropionate and Methyl 2-Chloro-3-cyanotrifluoropropionate

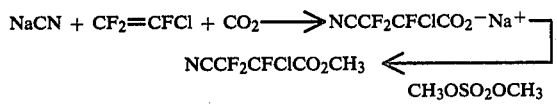

A reaction mixture of 24.5 g (0.50 mole) of NaCN, 33 g (0.75 mole) of $CO_2$, 58 g (0.50 mole) of chlorotrifluoroethylene, and 150 ml of DMSO was reacted in a 400 ml metal tube while warming from below 0°. The pressure went from 290 psi ($2.0 \times 10^3$ kPa) at 4° to 220 psi ($1.5 \times 10^3$ kPa) at 24° over a period of 20 hr., resulting in a mixture which contained sodium 2-chloro-3-cyanotrifluoropropionate.

Dimethyl sulfate (69.3 g, 0.55 mole) was added dropwise, and the resulting mixture was stirred for 3 hr. while the temperature was maintained in a cooling bath at less than 30°. Removal of volatiles under reduced pressure and fractionation yielded 64.9 g (64%) of methyl 2-chloro-3-cyanotrifluoropropionate, bp 57°–58° (50 mm, 6.7 kPa). IR ($CCl_4$): 3020, 2960, and 2950 (sat'd CH), 2250 (CN), 1770 (C=O), and 1100–1250 cm$^{-1}$ (CF, CO). NMR ($CCl_4$): $^1$H 3.95 ppm (s, $OCH_3$); $^{19}$F −132.9 ppm (t, $J_{FF}$ 13.6 Hz, 1 F$^4$, CF) with AB for $CF_2$ at −9283, −9570, −9633, and −9921 Hz (d, $J_{FF}$ 13.6 Hz 2F).

Anal. Calcd. for $C_5H_3ClF_3NO_2$: C, 29.80; H, 1.50; N, 6.95. Found: C, 30.04; H, 1.84; N, 6.96.

EXAMPLE 8

Sodium 3-Azidotetrafluoropropionate and Methyl 3-Azidotetrafluoropropionate

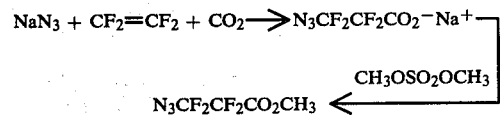

A 400 ml metal tube charged with 26.0 g (0.40 mole) of $NaN_3$, 33 g (0.75 mole) of $CO_2$, 50 g (0.50 mole) of TFE and 150 ml of DMSO was heated at 50° for 4 hr. while the pressure was allowed to drop from 730 psi ($5.0 \times 10^3$ kPa) to 520 psi ($3.6 \times 10^3$ kPa), and then at 100° for 2 hr. at about 765–800 psi ($5.3 \times 10^3$–$5.5 \times 10^3$ kPa), to give sodium 3-azidotetrafluoropropionate.

The reaction mixture was then stirred with 56.7 g (0.45 mole) of dimethyl sulfate until an initial exothermic reaction subsided. Volatiles were removed under reduced pressure and fractionated to give 73.2 g (91%) of methyl 3-azidotetrafluoropropionate, bp 54° (50 mm, 6.7 kPa). IR ($CCl_4$); 3010, 2960, and 2855 (sat'd CH); 2160 ($N_3$), 1785 (C=O) and 1100–1300 cm$^{-1}$ (CF, C—O). NMR ($CCl_4$): $^1$H 3.99 ppm (s, $OCH_3$); $^{19}$F −91.7 (t, $J_{FF}$ 4.7 Hz, 2F, $CF_2N_3$) and −120.5 ppm (t, $J_{FF}$ 4.7 Hz, 2F, $CF_2$ C=O).

Anal. Calcd. for $C_4H_3F_4N_3O_2$: C, 23.89, H, 1.50; N, 20.90. Found: C, 24.27; H, 1.71; N, 21.31.

EXAMPLE 9

Sodium 3-Azido-2-trifluoromethoxytrifluoropropionate and Methyl 3-Azido-2-trifluoromethoxytrifluoropropionate

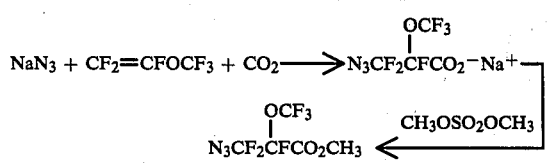

A mixture of 32.5 g (0.50 mole) of $NaN_3$, 33 g (0.75 mole) of $CO_2$, 83 g (0.50 mole) of trifluoromethyl trifluorovinyl ether, and 150 ml of dimethyl sulfoxide was reacted at 25°–27° and 380–280 psi ($2.6 \times 10^3$–$1.9 \times 10^3$ kPa) for 10 hr.

The resulting solution, which contained sodium 3-azido-2-trifluoromethoxytrifluoropropionate, was stirred with 69.3 g (0.55 mole) of dimethyl sulfate for 3 hr. until an initial exothermic reaction subsided. Volatiles were removed at 50° (2 mm, $2.6 \times 10^{-1}$ kPa), and the resulting crude ester was fractionated to yield 111.8 g (84%) of methyl 3-azido-2-trifluoromethoxytrifluoropropionate, bp 38°–41° (24 mm, 2.1 kPa). IR ($CCl_4$): 3010, 2960, and 2850 (sat'd CH); 2150 ($N_3$), 1780 (C=O), and 1100–1250 cm$^{-1}$ (C—F). NMR ($CCl_4$): $^1$H 3.89 ppm (s, $OCH_3$); $^{19}$F −56.0 (d, $J_{FF}$ 8.6 Hz, 3F, $OCF_3$) and −131.6 ppm (q of t, $J_{FF}$ 8.6, 5 Hz, 1F, CF) with an AB for $CF_2N_3$ at −8333 and −8521 Hz (d, $J_{FF}$ 5.0 Hz, 1F) and −8548 and −8763 Hz (d, $J_{FF}$ 5.6 Hz, 1F).

Anal. Calcd. for $C_5H_3F_6N_3O_3$: C, 22.49; H, 1.13; N, 15.73. Found: C, 22.81; H, 1.48; N, 16.00.

EXAMPLE 10

Sodium 3-Azido-2-heptafluoro-n-propoxytrifluoropropionate and Methyl 3-Azido-2-heptafluoro-n-propoxytrifluoropropionate

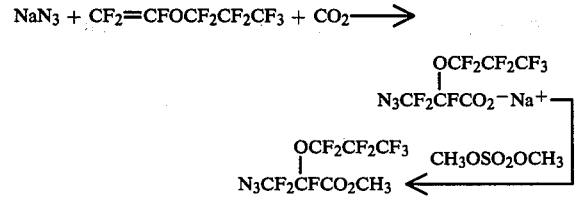

A reaction mixture of 26.0 g (0.40 mole) of $NaN_3$, 33 g (0.75 mole) of $CO_2$, 106 g (0.40 mole) of heptafluoro-n-propyltrifluorovinyl ether, and 150 ml of DMSO was shaken at 25° for 16 hr. in a 400 ml tube.

The resultant mixture, which contained sodium 3-azido-2-heptafluoro-n-propoxytrifluoropropionate, was treated with 56.7 g (0.45 mole) $CH_3OSO_2OCH_3$, stirred overnight, and then poured into 1.5 liter of cold water. The organic layer was washed with 500 ml of water, dried over $CaSO_4$, and distilled to yield 115.8 g (79%) of methyl-3-azido-2-heptafluoro-n-propoxy-trifluoropropionate, bp 44°–45° (10 mm, 1.3 kPa). IR ($CCl_4$); 3010, 2970, and 2850 (sat'd CH), 2150 ($N_3$), 1780 (C=O), and 1100–1250 cm$^{-1}$ (CF, C—O). NMR ($CCl_4$); $^1$H 3.92 ppm (s, $OCH_3$); $^{19}$F −82.1 (t, $J_{FF}$ 7.3 Hz, 3F, $CF_3$), −130.3 (d of d of t, $J_{FF}$ 19.6, 6, 6 Hz, 1F, CF), and −130.4 ppm (s, 2F, $CF_2$) with AB multipliers for $OCF_2$ at −7443 and −7592 Hz (d of q, $J_{FF}$ 19.6, 7.3 Hz, 1F) and −8189 and −8340 Hz (q of d, $J_{FF}$ 7.3, 6 Hz, 1F) and for $CF_2N_3$ at −8359, −8547, −8567 and −8757 Hz (d, $J_{FF}$ 6 Hz, 2F).

Anal. Calcd. for $C_7H_3F_{10}N_3O_3$: C, 22.90; H, 0.82; N, 11.45. Found: C, 22.45; H, 1.09; N, 11.70.

EXAMPLE 11

Sodium 3-t-Butylthiotetrafluoropropionate and Methyl 3-t-Butylthiotetrafluoropropionate

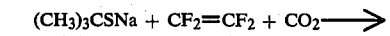

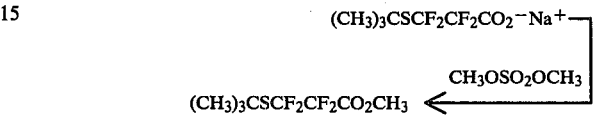

A suspension of 24 g (0.50 mole) of 50% NaH/mineral oil in 140 ml of DMSO was stirred and maintained at 45° while 45 g (0.50 mole) of t-butylmercaptan was added dropwise. The thick mixture was then stirred and heated at 45° for about 4.5 hr., until the evolution of hydrogen became extremely slow. The resulting slurry was rinsed into a 400 ml metal tube with 10 ml of DMSO, 0.33 g (0.75 mole) of $CO_2$ and 50 g (0.50 mole) of TFE were added, and the mixture was agitated at 100° for 8 hr.

The resulting dark solution, which contained sodium 3-t-butylthiotetrafluoropropionate, was stirred with 69.3 g (0.55 mole) of dimethyl sulfate while the temperature was maintained at 30°. After an initial exothermic reaction subsided, the mixture was stirred overnight and then distilled to give a crude product with bp about 45° (2 mm, $2.6 \times 10^{-1}$ kPa). The distillate was washed with 1 liter of water, dried and fractionated to give 52.1 g (42%) of methyl 3-t-butylthiotetrafluoropropionate, bp 55° (2 mm, $2.6 \times 10^{-1}$ kPa). IR (neat): 2970 (sat'd CH), 1775 (C=O), 1100–1250 cm$^{-1}$ (CF). NMR ($CCl_4$): $^1$H 3.87 (s, 3H, $OCH_3$) and 1.52 ppm (s, 9H, $C(CH_3)_3$); $^{19}$F −86.3 (t, $J_{FF}$ 7.1 Hz, 2F, $CF_2S$) and −117.6 ppm (t, $J_{FF}$ 7.1 Hz, 2F, $CF_2$C=O).

Anal. Calcd. for $C_8H_{12}F_4O_2S$: C, 38.71; H, 4.87. Found: C, 38.99; H, 5.05.

EXAMPLE 12

Sodium 3-dimethylphosphonotetrafluoropropionate and a Related Salt

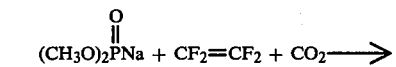

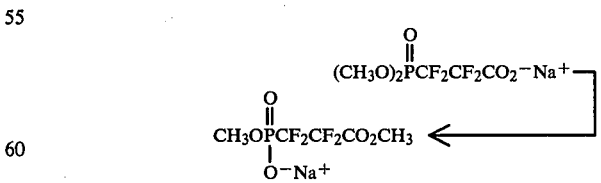

To a suspension of 24.0 g (0.50 mole) of 50% 55 g (0.50 mole) of dimethyl phosphite was added NaH/mineral oil in 150 ml of DMSO while the mixture was stirred. A pronounced foaming problem necessitated slow portion-wise additions and a prolonged reaction time after the phosphate addition had been completed.

The resulting mixture was heated in a 400 ml tube with 33 g (0.75 mole) of $CO_2$ and 50 g (0.50 mole) of TFE, first at 50° for 4 hr. and then at 100° for one hr. Removal of solvent from the resulting solution until the residue was at 75° (0.40 mm, $5.3 \times 10^{-2}$ kPa) gave 106 g of material which solidified on standing. IR (neat); 2950, 2920, and 2850 (sat'd CH), 1770 (ester C=O), 1690 and 1440 ($CO_2$)⁻, 1260 (P=O), and 1000–1200 cm⁻¹ (CF, P—O—C). NMR (DMSO): $^{19}F$ shows a 55:45 mixture; major component −118.9 (t, $J_{FF}$ 4.6 Hz, 2F, $CF_2C$=O) and −122.3 ppm (d of t, $J_{FP}$ 71 Hz, $J_{FF}$ 4.6 Hz, 24, $CF_2P$) and minor component −118.4 (broad s, 2F, $CF_2C$=O) and −123.3 ppm (broad d, $J_{FP}$ 72 Hz, 2F, $CF_2P$). The spectra indicate a mixture of $(CH_3O)_2$-$P(O)CF_2CF_2CO_2^-Na^+$ and

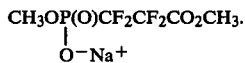

EXAMPLE 13

A. Methyltriethylammonium-3-cyanotetrafluoropropionate

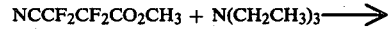

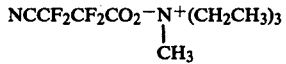

A homogeneous solution of 9.3 g (0.05 mole) of methyl 3-cyanotetrafluoropropionate prepared as in Example 3, and 5.1 g (0.05 mole) of triethylamine in 25 ml of ether was stirred at 25°. After 4 days, a second layer had slowly formed; no increase was observed during an additional 2 days. Removal of volatiles under full pump at 25° gave a deliquescent yellow solid, methyltriethylammonium-3-cyanotetrafluoropropionate, mp 52°–55°. IR ($CDCl_3$): 2965 (sat'd CH), 2255 (CN), 1690 ($CO_2$), and 1250–1100 cm⁻¹ (CF). NMR ($CDCl_3$): $^1H$ 3.47 (q, $J_{HH}$ 7.1 Hz, 6H, $CH_2$—N, 3.08 (s, 3H, $CH_3$—N), and 1.37 ppm (t, $J_{HH}$ 7.1 Hz, of m, 9H, $CH_3$); $^{19}F$ −108.5 (t, $J_{FF}$ 8.4 Hz, 2F, $CF_2CN$) and −119.3 ppm (t, $J_{FF}$ 8.4 Hz, 2F, $CF_2C$=O with only 3% of impurities present.

Further proof of structure was obtained from reactions of this material as described below. Subsequent preparations on a 0.2 to 0.34 mole scale gave 92–95% yields of methyltriethylammonium-3-cyanotetrafluoropropionate varying in purity from a slightly moist solid to a half liquid material at 25°.

B. 3-Cyanotetrafluoropropionyl Fluoride and Perfluoro-5-oxa-7-octenenitrile

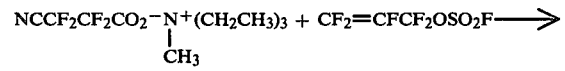

A solution of 53.9 g (0.2 mole) of methyltriethylammonium-3-cyanotetrafluoropropionate prepared as in Part A in 300 ml of diglyme was stirred at −10° to −5° while 46.0 g (0.20 mole) of perfluoroallyl fluorosulfate was rapidly added. The mixture was then stirred at −10° to −5° for 1 hr., and then at −5° to 0° for 4 hr.

Removal of volatiles at 35° (5 mm, $6.7 \times 10^{-1}$ kPa) through a liquid $N_2$ trap and fractionation gave 10.0 g (29%) of 3-cyanotetrafluoropropionyl fluoride, bp 19°–20°. IR (gas phase):2265 (CN), 1888 (COF), and 1300–1100 cm⁻¹ (CF) with traces of $CO_2$, $SO_2F_2$ and $SiF_4$ present. NMR ($CCl_4$; 0°); $^{19}F$ 25.8 (t of t, $J_{FF}$ 10.1, 5.0 Hz, 1F, COF), −106.7 (d of t, $J_{FF}$ 5.0, 4.6 Hz, 2F, $CF_2CN$), and −118.5 ppm (d of t, $J_{FF}$ 10.1, 4.6 Hz, 2F, $CF_2C$=O).

Further fractionation gave 3.9 g of recovered perfluoroallyl fluorosulfate, bp 62°–63°, and 8.0 g (12%) of perfluoro-5-oxa-7-octenenitrile, bp 81°–83°. IR ($CCl_4$): 2265 (CN), 1790 (C=C), and 1300–1100 cm⁻¹ (CF, C—O). NMR ($CCl_4$): −71.9 (d of d of t of d, $J_{FF}$ 25.2, 13.9, 11.6, 7.3 Hz, 2F, $OCF_2C$=), −83.7 (t of t of m, $J_{FF}$ 11.6, 9, 2F, $OCF_2$), −91.0 (d of d of t, $J_{FF}$ 50.8, 39.5, 7.3, Hz, 1F, cis—$CF_2CF$=CFF), −104.7 (d of d of t, $J_{FF}$ 118.0, 50.8, 25.2 Hz, 1F, trans—$CF_2CF$=CFF), −106.4 (t of t of d, $J_{FF}$ 8.8, 4.4., 1.6 Hz, 2F, $CF_2CN$), −127.5 (t of t, $J_{FF}$ 4.4, 2.3 Hz, 2F, $CF_2$), and −190.8 ppm (d of d of t of t, $J_{FF}$ 118.0, 39.5, 13.9, 1.6 Hz, 1F, $CF_2CF$=).

Anal. Calcd. for $C_7F_{11}NO$: C, 26.02; N, 4.34. Found: C, 26.36; N, 4.41.

C. Perfluoro-5-oxa-7-octenenitrile with Excess Fluorosulfate

Perfluoroallyl fluorosulfate (92.0 g, 0.40 mole) was added slowly to a mixture of 54.5 g (0.2 mole) of methyltriethylammonium-3-cyanotetrafluoropropionate prepared as in Part A, 11.6 g (0.20 mole) of flame-dried KF, and 300 ml of diglyme stirred at −10° to −5°. The mixture was then stirred at −10° to −5° for 3 hr. and poured into 1.5 liters of ice water. The lower layer was washed with 500 ml of cold water, dried over $CaSO_4$, and fractionated to give 21.9 g (34% from $NCCF_2CF_2CO_2CH_3$) of perfluoro-5-oxa-7-octenenitrile, bp 80°–84°, which was determined to be essentially pure by gas chromatography (GC). This example shows that a higher yield of the allyl ether results when an excess of fluorosulfate is used.

D. Perfluoro-5-oxa-7-octenenitrile and Copolymer

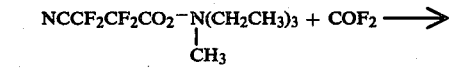

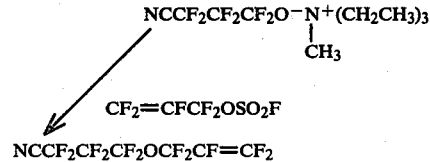

A solution of 54.2 g (0.2 mole) of methyltriethylammonium-3-cyanotetrahydropropionate prepared as in Part A in 300 ml of diglyme was stirred at −15° to −10° while 14 g (0.21 mole) of carbonyl fluoride was added slowly. The mixture was stirred at −15° to −10° for 30 min and then at −10° to −5° for 30 min, after which 50.6 g (0.22 mole) of perfluoroallyl fluorosulfate was added. The mixture was stirred at −5° to 0° for an additional hour and then poured into 1.5 liters of cold water. The lower layer was washed with 500 ml of water, dried over $CaSO_4$, and distilled to give 30.2 g (47% from NCCF$_2$CF$_2$CO$_2$CH$_3$) of perfluoro-5-oxa-7-octenenitrile, bp 80°–85°, identified by IR and GC.

15.8 g (0.049 mole) of NCCF$_2$CF$_2$CF$_2$OCF$_2$CF=CF$_2$, prepared as described above, and 20 ml of F-113 (1,1,2-trifluoro-1,2,2-trichloroethane) were mixed and cooled to 0°. 2 ml of 5% perfluoropropionyl peroxide in F-113 was added and the mixture was loaded into a 100 ml tube and pressured to 50 psi (345 kPa) at 20° with TFE. The temperature was raised to 40° and the pressure was increased to, and maintained at, 100 psi (689 kPa) with further TFE being added until reaction ceased after a period of about 6 hr. A total of 11.1 g (0.11 mole) of TFE was added.

37.5 g of moist white solid was recovered; after drying under vacuum to constant weight, 4.5 g of white polymer was obtained. Presence of pendant cyano groups in the polymer was confirmed by IR. 7.3 g (46%) of the starting cyanoolefin was recovered from the volatiles.

EXAMPLE 14

A. Methyltriethylammonium-3-azidotetrafluoroproprionate

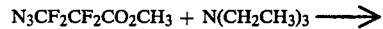

N$_3$CF$_2$CF$_2$CO$_2$CH$_3$ + N(CH$_2$CH$_3$)$_3$ ⟶

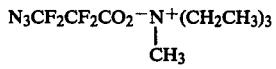

N$_3$CF$_2$CF$_2$CO$_2^-$N$^+$(CH$_2$CH$_3$)$_3$
              |
              CH$_3$

A mixture of 37.0 g (0.184 mole) of methyl-3-azidotetrafluoropropionate, prepared as in Example 9, 20.2 g (0.20 mole of triethylamine, and 50 ml of ether was stirred at 25°. A second layer slowly formed. The reaction was stopped after 24 days, at which time the second layer was not increasing in volume. Evaporation of volatiles under full pump vacuum left 54.9 g (99% of theory) of methyltriethylammonium 3-azidotetrafluoropropionate as a moist solid. IR(CHCl$_3$): 3020 (sat'd CH), 2170 (N$_3$), 1690 (CO$_2$), and 1250–1100 cm$^{-1}$ (CF). NMR (DMSO-d$_6$): $^1$H 3.31 (q, J$_{HH}$ 7 Hz, 6H, CH$_2$), 2.93 (s, 3H, NCH$_3$), and 1.22 ppm (t, J$_{HH}$ 7 Hz, 9H, CH$_3$); $^{19}$F −90.8 (t, J$_{FF}$ 6.3 Hz, 2F, CF$_2$N$_3$) and −115.6 ppm (t, J$_{FF}$ 6.3 Hz, 2F, CF$_2$C=O).

B. Perfluoro-4-oxa-6-heptenyl azide

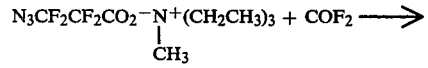

N$_3$CF$_2$CF$_2$CO$_2^-$N$^+$(CH$_2$CH$_3$)$_3$ + COF$_2$ ⟶
              |
              CH$_3$

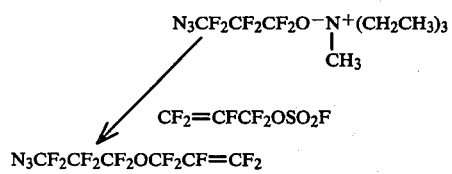

N$_3$CF$_2$CF$_2$CF$_2$O$^-$N$^+$(CH$_2$CH$_3$)$_3$
                    |
                    CH$_3$

CF$_2$=CFCF$_2$OSO$_2$F

N$_3$CF$_2$CF$_2$CF$_2$OCF$_2$CF=CF$_2$

An impure sample of methyltriethylammonium-3-azido tetrafluoropropionate prepared as described above (54.9 g, about 0.18 mole) was dissolved in 300 ml of diglyme and stirred at −20° to −15° while 13.5 g (0.20 mole) of COF$_2$ was passed in slowly enough to be completely absorbed. The mixture was stirred at 0° for 1 hr., after which 46.0 g (0.20 mole) of perfluoroallyl fluorosulfate was added rapidly at −5° to 0°. Resulting solids were broken up and the mixture was stirred at −5° to 0° for 1.5 hr., at 0° to 5° for 1 hr., and then was poured into 1.5 liters of cold water. The organic layer was washed with 200 ml of cold water, dried over CaSO$_4$, and distilled to give 21.3 g (35% from N$_3$CF$_2$CF$_2$CO$_2$CH$_3$) of perfluoro-4-oxa-6-heptenyl azide, bp 59°–60° (110 mm, 14.6 kPa). IR (CCl$_4$): 2160 (N$_3$), 1790 (C=C), 1250–1100 cm$^{-1}$ (CF, C—O). NMR (CCl$_4$): $^{19}$F −72.0 (d of d of t of d, J$_{FF}$ 25.0, 14.0, 12.3, 7.3 Hz, 2F, OCF$_2$=), −84.3 (t of t of m, J$_{FF}$ 12.3, 9 Hz, 2F, OCF$_2$CF$_2$), −89.6 (t of m, J$_{ff}$ 9 Hz, 2F, CF$_2$N$_3$, −92.0 (d of d of t, J$_{FF}$ 52.3, 39.1, 7.3 Hz, 1F, cis-CF$_2$CF=CFF), −105.3 (d of d of t, J$_{FF}$ 117.7, 52.3, 25.0 Hz, 1F, trans—CF$_2$CF=CFF), −128.3 (broad s, 2F, CF$_2$), and −190.5 ppm (d of d of t of t, J$_{FF}$ 117.7, 39.1, 14.0, 1.6 Hz, 1F, CF$_2$CF=).

Anal. Calcd. for C$_6$F$_{11}$N$_3$O: C, 21.25; N, 12.39. Found: C, 21.85; N, 12.86.

EXAMPLE 15

Copolymer of TFE and Perfluoro-4-oxa-6-heptenyl Azide 16.3 g (0.048 mole) of N$_3$(CF$_2$)$_3$OCF$_2$CF=CF$_2$, prepared as in Example 14B, and 20 ml of F-113 (1,1,2-trifluoro-1,2,2-trichloroethane) were mixed and cooled to 0°. 2 ml of 5% perfluoropropionyl peroxide in F-113 was added and the mixture was loaded into a 100 ml tube and pressured to 100 psi (689 kPa) at 22° with TFE (ca. 30 g added). The temperature was raised to 40° (pressure 160 psi, 1103 kPa). After 6 min, pressure had fallen to 110 psi (758 kPa). The mixture was then heated to 72°. After 10 min, the temperature and pressure had dropped to 42° and 80 psi (551 kPa). The flask was then repressured with TFE to 210 psi (1447 kPa). The total amount of TFE added was 40 g. The flask was held at 40° for 2.5 hr. The pressure fell to 70 psi (482 kPa) within 1 hr. and then remained constant.

52.4 g of a moist white solid was recovered. Volatiles were removed under vacuum to constant weight (1.5 days). 17.9 g of a white copolymer of TFE and perfluoro-4-oxa-6-heptenyl azide was obtained. Presence of pendant azido groups on the polymer was confirmed by IR. 11.2 g (69%) of N$_3$(CF$_2$)$_3$OCF$_2$CF=CF$_2$ was recovered from the volatiles.

EXAMPLE 16

Tetramethylammonium-3-azidotetrafluoropropionate

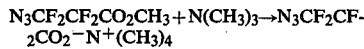

N$_3$CF$_2$CF$_2$CO$_2$CH$_3$+N(CH$_3$)$_3$→N$_3$CF$_2$CF$_2$CO$_2^-$N$^+$(CH$_3$)$_4$

Trimethylamine (10.6 g, 0.18 mole) was distilled into a solution of 37.0 g (0.184 mole) of methyl 3-azidotetrafluoropropionate, prepared as in Example 9, in 100 ml of ether. Precipitation of product was accompanied by a small exotherm. The reaction was determined by gas chromatography to be nearly complete after 4 hr. The mixture was stirred overnight, then evaporated under vacuum until dry. The residue was 31.8 g (68%) of tetramethylammonium-3-azidotetrafluoropropionate, mp 144°–145° (dec.). IR (nujol): 2170 (N$_3$), 1680 (broad, CO$_2$$^{1-}$), and 1250–1100 cm$^{-1}$ (CF), NMR (DMSO-d$_6$): H 3,25 ppm (s, CH$_3$); $^{19}$F −90.8 (t, J$_{FF}$ 6.2 Hz, 2F, CF$_2$N$_3$) and −115.8 ppm (t, J$_{FF}$ 6.2 Hz, 2F, CF$_2$C=O).

Anal. Calcd for C$_7$H$_{12}$F$_4$N$_4$O$_2$: C, 32.31; H,, 4.65; N, 21.53. Found: C, 32.23; H, 4.56; N, 21.30.

The propionate salt may be converted to a derivative or copolymer of the invention, e.g., as illustrated by Examples 14B and 15, above.

EXAMPLE 17

Sodium 3-methylthio-2,2,3,3-tetrafluoropropionate and the Methyl Ester

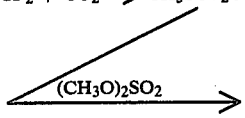

$CH_3SNa + CF_2=CF_2 + CO_2 \longrightarrow CH_3SCF_2CF_2CO_2Na$ $(CH_3O)_2SO_2 \longrightarrow$ $CH_3SCF_2CF_2CO_2CH_3$ A slurry of 24 g (0.50 mole) of 50% NaH/mineral oil in 140 ml of dry dimethyl sulfoxide was stirred while 24 g (0.50 mole) of methyl mercaptan was distilled in over a 2 hr. period. The mixture was then stirred until gas evolution became very slow after which the mixture was allowed to stand overnight. The resulting mixture was a thick paste which was diluted with 50 ml of dimethyl sulfoxide and charged into a 400 ml metal tube along with 33 g (0.75 mole) of carbon dioxide and 50 g (0.50 mole) of tetrafluoroethylene. The tube was shaken at 100° for 4 hr. The resulting solution was treated with 69.3 g (0.55 mole) of dimethyl sulfate. After an initial exotherm (maximum temperature, 50°), the mixture was stirred for 3 hr. Product was then removed under vacuum and fractionated to afford 63.9 g (62%) of methyl 3-methylthio-2,2,3,3-tetrafluoropropionate, bp 53° (10 mm, 1.3 kPa), IR (neat): 3020, 2970, and 2860 (satd CH), 1780 (C=O), and 1250-1100 cm$^{-1}$(C—F), $^1$H and $^{19}$F NMR agreed with the assigned structure.

Anal. Calcd for $C_5H_6F_4O_2S$: C, 29.13; H, 2.93; F, 36.86. Found: C, 29.42; H, 3.07; F, 36.74.

EXAMPLE 18

Methyl 3-Dimethoxyphosphonyltetrafluoropropionate

To 106 g of a crude preparation of sodium 3-dimethylphosphonyltetrafluoropropionate, prepared as in Example 12, was added an excess, 229 g (1.5 mole), of $POCl_3$. The mixture was warmed to 60° C., resulting in an exothermic reaction. After the reaction had subsided, solids were removed by filtration and rinsed with $CCl_4$. The filtrate and rinsings were distilled to remove volatiles, leaving 56.7 g of a heavy oil. The oil was stirred overnight with 50 ml of methanol, and the methanol layer was separated and distilled to give 5.5 g of a liquid, bp 60°-66° (0.4 mm, 5.3×10$^{-2}$ kPa). NMR ($CD_3CN$): $^1$H 3.98 (s, 3H, C(=O)OCH$_3$) and 3.90 ppm (d, $J_{HP}$7 Hz, 6H, P—OCH$_3$) with bands for $(CH_3O)_3P=O$ also present; $^{19}F$ −118.7 (t, $J_{FF}$ 2.9 Hz, 2F, $CF_2C$=O) and −121.5 ppm (d, $J_{FF}$ 88.6 Hz, of t, $J_{FF}$ 2.9 Hz, 2F, $CF_2$—P). IR (neat) showed no P—OH or C—OH and indicated a mixture of $(CH_3O)_2P(O)CF_2CF_2CO_2CH_3$ and $(CH_3O)_3P=O$.

EXAMPLE 19

3-Dichlorophosphonyltetrafluoropropionyl Chloride

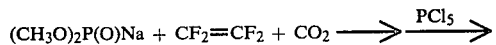

$(CH_3O)_2P(O)Na + CF_2=CF_2 + CO_2 \xrightarrow{PCl_5}$ $Cl_2\overset{O}{\overset{\|}{P}}CF_2CF_2\overset{O}{\overset{\|}{C}}Cl$ A. A stirred suspension of 24.0 g (0.50 mole) of 50% NaH/mineral oil in 150 ml of dimethyl sulfoxide was treated portionwise with 55 g (0.50 mole) of dimethyl phosphite. When gas evolution ceased, the suspension of sodium dimethyl phosphite was charged into a 400-ml metal tube, after which 33 g (0.75 mole) of $CO_2$ and 50 g (0.50 mole) of tetrafluoroethylene was added at 13°. Reaction was carried out at 25° for 4 hours, then at 50° for 8 hours. The reaction mixture was stirred into a solution of 200 ml of concentrated $H_2SO_4$ in 1 liter of water, and the resulting solution was extracted continuously with ether for 30 hr. Volatiles were removed from the extracts to produce 51 g of an oil, which was added to 416 g (2.0 moles) of phosphorous pentachloride. The mixture was heated slowly to reflux, at which point gas evolution substantially ceased. The residue was heated to 40° (1.6 mm, 2.1×10$^{-1}$ kPa) to transfer volatiles to a cold trap. Fractionation of the volatiles gave 5.7 g (4% yield from $CF_2=CF_2$) of crude 3-dichlorophosphonyltetrafluoropropionyl chloride, bp 90°-115° (100 mm, 13.3 kPa). IR ($CCl_4$): 1800 (C=O), 1310 (P=O), and 1250-1100 cm$^{-1}$ (CF).NMR($CCl_4$): $^{19}$F −110.6 (m, 2F, $CF_2C$=O) and −116.0 ppm (d, $J_{FP}$ 113 Hz, of t, $J_{FF}$2.3 Hz, 2F, $CF_2$—P). Mass spec: m/e 245(M$^+$—Cl), 217(M$^+$—COCl), 117($POCl_2^+$), 113($CLCOCF_2^+$), 100($C_2F_4^+$), and 63($COCl^+$) with the expected Cl isotope peaks present. The main impurity was shown to be $CH_3SCCl_3$.

B. The reaction of Part A was carried out in tetrahydrofuran at 50°-100°. Evaporation of solvent, treatment of the residue with $PCl_5$, and fractionation gave 4.3 g (3%) of 3-dichlorophosphonyltetrafluoropropionyl chloride, bp 47°-49° (10 mm, 1.3 kPa).

C. Reaction of excess sodium diethyl phosphite in dimethyl sulfoxide with $CO_2$ and tetrafluoroethylene at 50°-100° led, after the treatment with $PCl_5$, to a 14% yield of 3-dichlorophosphonyltetrafluoropropionyl chloride, bp 59°-69° (20 mm, 2.6 kPa).

EXAMPLE 20

A. 3-Azido-2-heptafluoropropoxytrifluoropropionyl Fluoride and Adducts with Hexafluoropropene Oxide $NaN_3 + CF_2=CFOCF_2CF_2CF_3 + CO_2 \longrightarrow$

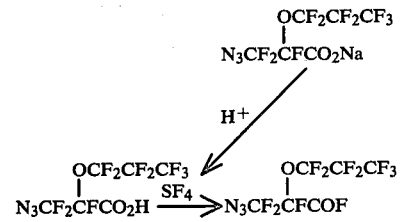

Reaction of 26.0 g (0.40 mole) of sodium azide, 33 g (0.75 mole) of carbon dioxide, and 106 g (0.40 mole) of perfluoro(propyl vinyl ether) in dimethyl sulfoxide was carried out in a 400 ml metal tube at 25°. The reaction mixture was poured into a solution of 250 ml of concentrated sulfuric acid in 900 ml of water. Continuous extraction with ether and evaporation of the extracts afforded 140 g of crude 3-azido-2-heptafluoropropoxytrifluoropropionic acid hydrate. This acid was reacted in a 1L metal tube under autogenous pressure with 150 g (1.39 moles) of $SF_4$ and 84 g (2.0 moles) of NaF in 80 ml of $CFCl_2CF_2Cl$ at 80° for 12 hr. Distillation gave 82.9 g (58% overall yield) of 3-azido-2-heptafluoropropoxytrifluoropropionyl fluoride, bp 51°-53° (100 mm, 13.3 kPa). IR (CCl$_4$): 2150 (N$_3$), 1875 (COF), and 1300-1100 cm$^{-1}$ (CF, C—O). NMR (CCl$_4$): $^{19}$F 26.0 (p, J$_{FF}$ 6 Hz, 1F, COF), −82.0 (t, J$_{FF}$7.5 Hz, 3F, CF$_3$), −129.3 (d of p, J$_{FF}$20, 6 Hz, 1F, CF), and −130.2 ppm (s, 2F, CF$_2$) with an AB pattern for CF$_2$O at −7417 and −7567 Hz (d of q, J$_{FF}$20, 7.5 Hz, 1F) and −8181 and −8332 Hz (q, J$_{FF}$7.5 Hz, 1F), and for CF$_2$N$_3$ at −8244 and −8430 Hz (t, J$_{FF}$ 5.5 Hz, 1F) and −8465 and −8651 Hz (t,J$_{FF}$ 6.2 Hz, 1F).

B.

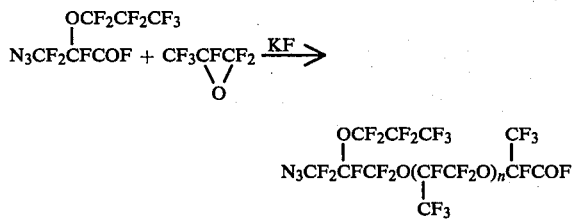

The acid fluoride (72 g; 0.20 mol) prepared in Part A was added to a suspension of 10.0 g (0.17 mole) of flame-dried KF and 100 ml of 9:1 adiponitrile/tetraglyme. The system was evacuated and an atmosphere of pure hexafluoropropene was introduced. The mixture was stirred while 67 g (0.40 mole) of hexafluoropropene epoxide was added on demand at 1 atm (1.0×10$^2$ kPa) over a period of 2 hr. The temperature rose slowly from 20° to 42°. Distillation up to bp 50° (0.3 mm, 4.0×10$^{-2}$ kPa) afforded 135.9 g of volatiles, which were then fractionated. The 1:1 adduct (n=0) was obtained as 35.0 g (34%) of oil, bp 46°-47.5° (9.5 mm, 1.3 kPa), IR (neat): 2170 (N$_3$), 1890 (COF), and 1300-1100 cm$^{-1}$ (CF,C—O). The $^{19}$F NMR spectrum was compatible with N$_3$CF$_2$CF(OCF$_2$CF$_2$CF$_3$)CF$_2$OCF(CF$_3$)COF.

Anal. Calcd. for C$_9$F$_{17}$N$_3$O$_3$:C,20.74;N,8.06 Found: C,20.47; N,8.14

The 2:1 adduct (n=1) was obtained as 5.2 g (4%) of oil, bp 43°-46° (1.2 mm, 1.6×10$^{-1}$ kPa). IR (neat): 2170(N$_3$), 1890 (COF), and 1300-1100 cm$^{-1}$(CF,C—O). The $^{19}$F NMR spectrum was compatible with N$_3$CF$_2$CF(OCF$_2$CF$_2$CF$_3$)CF$_2$OCF(CF$_3$)COF.

Anal. Calcd. for C$_{12}$F$_{23}$N$_3$O$_4$:C,20.98;N,6.12 Found: C,21.26;N,6.39

EXAMPLE 21

9-Azido-8-heptafluoropropoxy-5-trifuoromethylun-decafluoro-3,6-dioxanonene-1

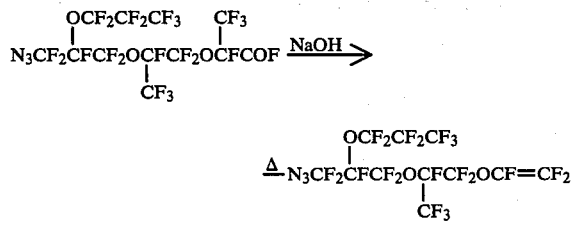

The 2:1 adduct (n=1) (18.0 g, 0.026 mole) prepared as in Example 20 was stirred with 50 ml of water while aqueous NaOH was added to a phenolphthalein end-point. The bulk of the volatiles were removed in a stream of air, and the product salt was dried at 140° (0.1 mm, 1.3×10$^{-2}$ kPa). Pyrolysis of the salt was carried out at 220°-235° over a 5 hr period, during which time the pressure went from 1.8 mm (2.4×10$^{-1}$ kPa) to 0.1 mm (1.3×10$^{-2}$ kPa). The crude product, which was collected in a cold trap, was washed with water, dried over calcium sulfate, and fractionated to give 7.7 g (48%) of the trifluorovinyl ether, bp 64°-68° (9.5 mm, 1.3 kPa). IR (neat): 2150 (N$_3$), 1835 (C=C), and 1300-1100 cm$^{-1}$ (CF, C=O).

Anal. Calcd. for C$_{11}$F$_{21}$N$_3$O$_3$:C,21,27;N,6.76 Found: C,21.10; N,6.88

EXAMPLE 22

Copolymer of TFE and N$_3$CF$_2$CF(OCF$_2$CF$_2$CF$_3$)CF$_2$OCF(CF$_3$)C-F$_2$OCF=CF$_2$ A cold (0°) solution of 7.3 g (0.012 mole) of the trifluorovinyl ether prepared in Example 21, 3 ml of 3% perfluoropropionyl peroxide in CFCl$_2$CF$_2$Cl, and 20 ml of CFCl$_2$CF$_2$Cl was loaded into a 100-ml metal tube and shaken at 25°-30° while 25 g (0.25 mole) of tetrafluoroethylene was added in portions. The reaction was then run at 40° for 2 hr. The polymer produced was suspended twice in CFCl$_2$CF$_2$Cl and filtered, then dried under high vacuum to give 3.3 g of the title copolymer as a white solid. IR (nujol): 2150 cm$^{-1}$ band for N$_3$ present.

EXAMPLE 23

A. Sodium 3-Methylsulfonyltetrafluoropropionate, 3-Methylsulfonyltetrafluoropropionic Acid and the Methyl Ester

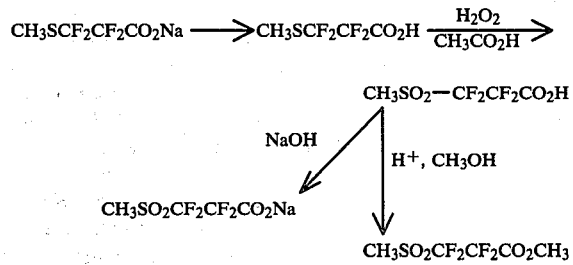

NaSCH$_3$ was prepared by distilling 24 g (0.50 mol) of methyl mercaptan into a stirred suspension of 24 g (0.50 mol) of 50% NaH/mineral oil in 170 ml of dimethyl sulfoxide over a 2-hr period. The mixture was charged into a 400-ml tube with 27 g (0.6 mol) of CO$_2$ and 50 g (0.50 mol) of tetrafluoroethylene and shaken at 50° for 8 hrs. The reaction mixture was poured into a cold solution of 300 ml of concentrated HCl in 1 liter of water, and the resulting mixture was extracted continuously with ether. Removal of volatiles from the extracts at 5 mm gave 94.6 g of 3-methylthiotetrafluoropropionic acid. This acid was stirred at 85° to 95° while a mixture of 125 ml (about 1.2 mol) of 30% H$_2$O$_2$ and 75 ml of acetic acid was added dropwise over 2 hrs. The mixture was stirred at 90° to 95° for 3 hrs more, then evacuated at full pump to remove volatiles.

The residual oil was extracted with pentane to remove mineral oil, then either treated with aqueous NaOH to reform the sodium salt, or esterified. The methyl ester was prepared by refluxing the acid 1 hr with 500 ml of methanol and 2 ml of concentrated HCl. Chloroform (500 ml) was added, the mixture was distilled to a high temperature of 63°. Another 500 ml of methanol and 1 ml of concentrated HCl were added, and the esterification allowed to proceed at 25° for 3 days. Chloroform (500 ml) was added and the mixture was fractionated to give 64.0 g (54% from TFE) of methyl 3-methylsulfonyltetrafluoropropionate, bp 75° (1.2 mm) IR (neat): 3020, 2970, 2940 and 2860 (sat'd CH) 1780 (C=O) 1355 (SO$_2$) and 1250–1100 cm$^{-1}$(CF, C—O, SO$_2$). NMR(CDCl$_3$): $^1$H 3.99 (s, 3H, CH$_3$O) and 3.16 ppm (t of t, $J_{HF}$1.8, 0.7 Hz, 3H, CH$_3$SO$_2$); $^{19}$F—116.4 (t of t, $J_{FF}$3.8 Hz, of t, $J_{HF}$ 2 Hz, 2F, CF$_2$SO$_2$) and −117.5 ppm (t, $J_{FF}$3.8 Hz, 2F, CF$_2$C=O). Anal. Calcd. for C$_5$H$_6$F$_4$O$_4$S: C, 25.22; H, 2.54. Found: C, 25.49; H, 2.98

B. Tetramethylammonium 3-Methylsulfonyltetrafluoropropionate

Trimethylamine (12.4 g, 0.21 mol) was distilled into a stirred solution of 47.8 g (0.20 mol) of methyl 3-methylsulfonyltetrafluoropropionate in 100 ml of ether. The mixture was stirred overnight, filtered under nitrogen, and the solid dried under vacuum. There was thus obtained 52.1 g (88%) of tetramethylammonium 3-methylsulfonyltetrafluoropropionate, mp 98° to 100°, as deliquescent crystals. NMR (DMSO-d$_6$): $^1$H 3.40 (t, $J_{HF}$2 Hz, 3H, CH$_3$SO$_2$) and 3.17 ppm (s, 12H, (CH$_3$)$_4$N$^+$); $^{19}$F—112.3 (t, $J_{FF}$3.0 Hz, 2F, CF$_2$C=O) and −114.4 ppm (t, $J_{FF}$3.0 Hz, of m, 2F, CF$_2$SO$_2$). Anal. Calcd. for C$_8$H$_{15}$F$_4$NO$_4$S: C, 32.32; H, 5.09; N, 4.7. Found: C, 32.20; H, 5.17; N, 4.44.

INDUSTRIAL APPLICABILITY

The propionate salts and derivatives of the invention are useful as intermediates to tetrafluorosuccinic acid, perfluorobutyrolactone and fluorinated functional allyl and vinyl ethers which can provide cure-sites or ion-exchange groups in fluorinated polymers, such as the copolymers of the invention which are moldable into shaped objects, e.g., ion-exchange membranes.

While preferred embodiments of the invention are illustrated and described by the above, it is to be understood that the invention is not limited to the precise embodiments herein disclosed and that the right to all changes and modifications which are within the scope of the following claims is reversed.

I claim:

1. A β-substituted fluoropropionate salt having the formula:

$$(XCF_2CFYCO_2)_nM$$

wherein
X is —N$_3$;
Y is —Cl, —F, —Br or —OR$_F$;
R$_F$ is perfluoroalkyl, branched or linear, having 1–10 carbon atoms or such perfluoroalkyl having one or more carbon-carbon links interrupted by ether oxygen;
M is alkali metal, alkaline earth metal or —NR$^1$R$^2$R$^3$R$^4$, wherein R$^1$–R$^4$ are, independently, C$_{1-6}$ linear alkyl, allyl or benzyl; and
n is the valence of M and is 1 or 2.

2. The salt of claim 1 wherein Y is —F.

3. The salt of claim 1 wherein M is sodium or —NR$^1$R$^2$R$^3$R$^4$ and n is 1.

4. The salt of claim 2 wherein M is —NR$^1$R$^2$R$^3$R$^4$ and n is 1.

5. The salt of claim 4 wherein R$_1$–R$_4$ are C$_{1-6}$ linear alkyl.

6. The salt of claim 5 wherein R$_1$–R$_4$ are methyl.

7. The substituted fluorocarbon having the formula:

$$X'CF_2CFYZ$$

wherein
X' is —N$_3$;
Y is —Cl, —F, —Br or —OR$_F$;
R$_F$ is perfluoroalkyl, branched or linear, having 1–10 carbon atoms or such perfluoroalkyl having one or more carbon-carbon links interrupted by ether oxygen;
Z is —COCl, —CO$_2$R'', —CO$_2$H,

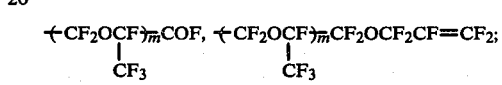

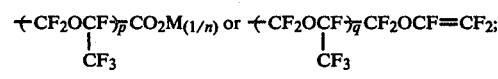

R'' is C$_{1-6}$ linear alkyl, allyl or benzyl;
m is 0 to 6;
p is 1 to 6; and
q is 0 or 1 to 5.

8. The substituted fluorocarbon of claim 7 wherein Y is —F.

9. The substituted fluorocarbon of claim 8 wherein Z is —CO$_2$R''.

10. The substituted fluorocarbon of claim 8 wherein Z is

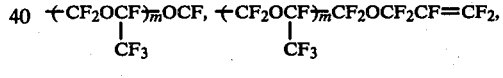

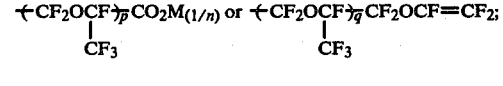

and m is 0 or 1 to 4.

11. The substituted fluorocarbon of claim 8 wherein Z is

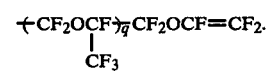

12. The substituted fluorocarbon of claim 8 wherein Z is

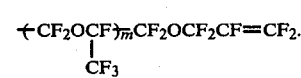

* * * * *